US00PP18082P2

(12) United States Plant Patent
Kurowski et al.

(10) Patent No.: US PP18,082 P2
(45) Date of Patent: Sep. 25, 2007

(54) BARBERRY PLANT NAMED 'MARIA'

(50) Latin Name: *Berberis thunbergii*
Varietal Denomination: Maria

(75) Inventors: Lucjan Kurowski, Konskowola (PL); Grzegorz Kurowski, Konskowola (PL)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 11/323,163

(22) Filed: Dec. 30, 2005

(51) Int. Cl.
*A01H 5/00* (2006.01)

(52) U.S. Cl. ..... Plt./241

(58) Field of Classification Search ..... Plt./241, Plt./226, 263
See application file for complete search history.

(56) References Cited

PUBLICATIONS

GTITM UPOVROM Citation for 'Maria' as per PL PBR BEA0002; Jun. 10, 2002.*

* cited by examiner

*Primary Examiner*—Kent Bell
(74) *Attorney, Agent, or Firm*—C. A. Whealy

(57) ABSTRACT

A new and distinct cultivar of Barberry plant named 'Maria', characterized by its upright and columnar plant habit; freely basally branching growth habit; distinct bright yellow to yellow green-colored leaves; and resistance to leaf scorch.

1 Drawing Sheet

Botanical designation: *Berberis thunbergii.*
Cultivar denomination: 'Maria'.

BACKGROUND OF THE INVENTION

The present Invention relates to a new and distinct cultivar of Barberry plant, botanically known as *Berberis thunbergii,* and hereinafter referred to by the name 'Maria'.

The new Barberry is a product of a planned breeding program conducted by the Inventors in Kuroska, Poland. The objective of the breeding program was to create new Barberry cultivars with new plant forms and unique foliage colors.

The new Barberry originated from an open pollination in 1998 of the *Berberis thunbergii* cultivar Aurea, not patented, as the female, or seed, parent with an unknown selection of *Berberis thunbergii,* as the male, or pollen, parent. The cultivar Maria was discovered and selected by the Inventors in 2001 as a single plant from within the progeny of the stated open pollination in a controlled environment in Kuroska, Poland.

Asexual reproduction of the new cultivar by softwood cuttings since 2001 in Kuroska, Poland, has shown that the unique features of this new Barberry are stable and reproduced true to type in successive generations.

SUMMARY OF THE INVENTION

Plants of the cultivar Maria have not been observed under all possible environmental conditions. The phenotype may vary somewhat with variations in environment such as temperature and light intensity without, however, any variance in genotype.

The following traits have been repeatedly observed and are determined to be the unique characteristics of 'Maria'. These characteristics in combination distinguish 'Maria' as a new and distinct Barberry cultivar:

1. Upright and columnar plant habit.
2. Freely basally branching growth habit.
3. Distinct bright yellow to yellow green-colored leaves.
4. Leaves resistant to scorch.

Plants of the new Barberry are most similar to plants of the female parent, the cultivar Aurea. In side-by-side comparisons conducted in Kuroska, Poland, plants of the new Barberry differed from plants of the cultivar Aurea in the following characteristics:

1. Plants of the new Barberry were more columnar and upright than plants of the cultivar Aurea.
2. Plants of the new Barberry were resistant to leaf scorch whereas plants of the cultivar Aurea were susceptible to leaf scorch.

Plants of the new Barberry can be compared to plants of the Barberry cultivar Helmond Pillar, not patented. In side-by-side comparisons conducted in Kuroska, Poland, plants of the new Barberry differed from plants of the cultivar Helmond Pillar in the following characteristics:

1. Plants of the new Barberry were broader than plants of the cultivar Helmond Pillar.
2. Plants of the new Barberry were more freely branching than plants of the cultivar Helmond Pillar.
3. Plants of the new Barberry had shorter leaves than plants of the cultivar Helmond Pillar.
4. Plants of the new Barberry had bright yellow to yellow green-colored leaves whereas plants of the cultivar Helmond Pillar had burgundy-colored leaves.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Barberry.

The photograph at the bottom of the sheet comprises a side perspective view of a typical plant of 'Maria' grown in an outdoor nursery.

The photograph at the top of the sheet is a close-up view of typical leaves of 'Maria'.

DETAILED BOTANICAL DESCRIPTION

Plants used in the aforementioned photographs and the following description were grown in containers under conditions which closely approximate commercial production conditions in Grand Haven, Mich. During the winter, plants were grown in a polyethylene-covered greenhouse and during the summer, plants were grown in a polypropylene-covered shadehouse. Plants were about three years old when the photographs and description were taken. In the following description, color references are made to The Royal Horticultural Society Colour Chart, 1995 Edition, except where general terms of ordinary dictionary significance are used.

Botanical classification: *Berberis thunbergii* cultivar Maria.

Parentage:

*Female, or seed, parent.*—*Berberis thunbergii* cultivar Aurea, not patented.

*Male, or pollen, parent.*—Unknown selection of *Berberis thunbergii,* not patented.

Propagation:

*Type.*—By softwood cuttings.

*Time to initiate rooting.*—About two weeks at 27° C.

*Time to produce a rooted young plant.*—About five months.

*Time to produce a rooted young plant.*—About five months.

*Root description.*—Fibrous, fleshy; color, 154B.

*Rooting habit.*—Freely branching; dense.

Plant description:

*Plant and growth habit.*—Perennial shrub. Upright and columnar plant habit. Freely branching habit; about 22 lateral branches per plant; pinching enhances branching; dense and bushy plant habit. Vigorous growth habit.

*Plant height.*—About 46 cm.

*Plant width.*—About 31 cm.

*Lateral branch description.*—Length: About 31 cm. Diameter: About 3.5 mm. Internode length: About 1.1 cm. Strength: Strong. Texture: Smooth, glabrous. Color, immature: 144B or occasionally, 46B. Color, mature: 144B. Thorns: Size: About 7 mm by 0.5 mm. Shape: Aciculate. Texture: Smooth, glabrous. Color, immature and mature: 144B.

*Foliage description.*—Leaf scorch: Leaves of the new Barberry are resistant to leaf scorch, a common problem with yellow-colored Barberries. Arrangement: Alternate, simple. Length: About 2.5 cm. Width: About 1.8 cm. Shape: Broadly ovate to spatulate. Apex: Obtuse to acute. Base: Attenuate to truncate. Margin: Entire. Texture, upper and lower surfaces: Smooth, glabrous. Venation pattern: Pinnate. Color: Developing foliage, upper surface: Shade, 154B; full sun, 8A, often flushed with 46A. Developing foliage, lower surface: 149A. Fully expanded foliage, upper surface: Shade, 154A; full sun, 8A; venation, similar to lamina. Fully expanded foliage, lower surface: 149A; venation, similar to lamina. Petiole length: About 1 cm. Petiole diameter: About 1 mm. Petiole texture, upper and lower surfaces: Smooth, glabrous. Petiole color, upper and lower surfaces: Similar to lamina.

Flower description: Flower development on plants of the new Barberry has not been observed.

Disease/pest resistance: Plants of the new Barberry have not been noted to be resistant to pathogens and pests common to Barberry.

Temperature tolerance: Plants of the new Barberry have been observed to tolerate temperatures from about −29° C. to about 35° C.

It is claimed:

1. A new and distinct cultivar of Barberry plant named 'Maria', as illustrated and described.

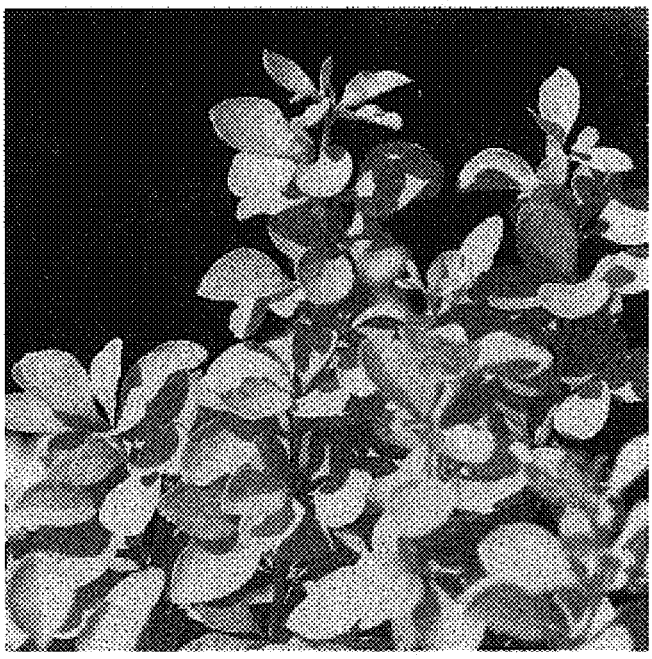
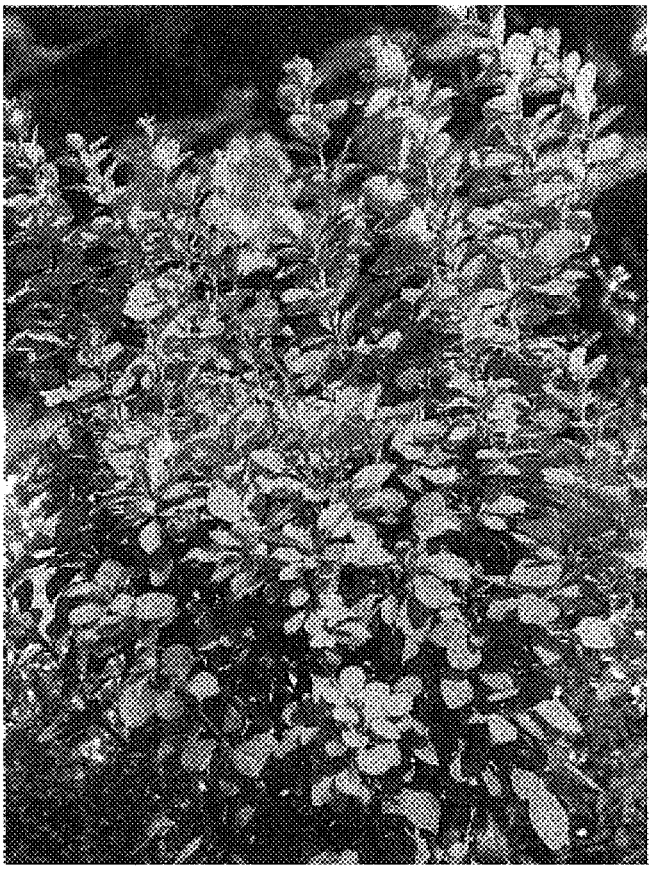

* * * * *